United States Patent [19]

Van Der Puy et al.

[11] 4,244,891

[45] Jan. 13, 1981

[54] PREPARATION OF HEXAFLUOROISOBUTYLENE

[75] Inventors: Michael Van Der Puy, Cheektowaga; Louis G. Anello, Hamburg; Bernard Sukornick, Williamsville; Richard F. Sweeney, Elma; Robert A. Wiles, Hamburg, all of N.Y.

[73] Assignee: Allied Chemical Corporation, Morris Township, Morris County, N.J.

[21] Appl. No.: 106,327

[22] Filed: Dec. 21, 1979

[51] Int. Cl.$^3$ ............................................. C07C 17/00
[52] U.S. Cl. .................................................. 570/140
[58] Field of Search ...................................... 260/653.3

[56] References Cited

U.S. PATENT DOCUMENTS 3,894,097   7/1975   Vanderkooi .................... 260/653.3

Primary Examiner—Delbert E. Gantz
Assistant Examiner—Joseph A. Boska
Attorney, Agent, or Firm—Jay P. Friedenson; Alan M. Doernberg

[57] ABSTRACT

The process for preparing hexafluoroisobutylene which comprises reacting, at elevated temperatures, ketene or a ketene-generating compound with hexafluorothioacetone. Hexafluoroisobutylene is a known valuable monomer which forms polymers of exceptional thermal, chemical and mechanical properties, particularly when copolymerized, such as with vinylidene fluoride.

10 Claims, No Drawings

PREPARATION OF HEXAFLUOROISOBUTYLENE

DESCRIPTION

1. Field of the Invention

This invention relates to a process for the preparation of hexafluoroisobutylene by reacting, at elevated temperature, ketene or a ketene generating compound with hexafluorothioacetone.

2. Background of the Invention

Hexafluoroisobutylene is a known compound whic is known to be useful for a variety of purposes such as, for example, a comonomer which forms polymers of exceptional thermal, chemical and mechanical properties with other comonomers such as vinylidene fluoride. The preparation of such copolymers is described in U.S. Pat. No. 3,706,723 to Chandrasekeran et al., issued Dec. 19, 1972. Hexafluoroisobutylene has been previously prepared by methods which include the reaction of hexafluoroacetone with ketene, the reaction of antimony trifluorodichloride with a chlorofluoroisobutylene and the dehydration of hexafluoro-2-methyl-2-propanol with phosphorus pentachloride or with sulfur tetrafluoride. These preparation and others suffer from one or more disadvantages from a commercial standpoint. For example, although the preparation involving hexafluoroacetone is a high-yield process, hexafluoroacetone represents a starting material of high cost and limited availability. The chlorofluoroisobutylene route involves several steps including a slow dehydrochlorination step, while the dehydration of the fluorinated tertiary butyl alcohol requires excessively long reaction times or expensive reagents.

It is accordingly an object of the invention to provide a new route to hexafluoroisobutylene which utilizes cheaper and more readily accessible starting materials.

Other objects and advantages of the invention will become apparent from the following description.

SUMMARY OF THE INVENTION

It has been found that hexafluoroisobutylene may be conveniently and cheaply prepared by reacting, at elevated temperatures, ketene or a ketene generating compound with hexafluorothioacetone.

DETAILED DESCRIPTION OF THE INVENTION AND OF THE PREFERRED EMBODIMENTS

The ketene reactant may be ketene or a ketene-generating compound, that is to say a compound which will generate ketene in the reactant system and make it available for reaction with the hexafluorothioacetone reactant. Generally, compounds which generate ketene are those which decompose to produce ketene when heated to a temperature in a range of about 340° to 1000° C. Exemplary of such compounds are acetyl-containing organic compounds such as acetic anhydride, acetone, acetic acid, isopropenyl acetate, acetyl acetone and the like, diketene and mixtures of two or more of any such compounds. The preferred ketene-generating compounds are acetic anhydride and diketene.

Hexafluorothioacetone is a known compound (b.p. 6° C.) and is a relatively reactive and unstable monomer. It is convenient to handle this compound in the form of its dimer 2,2,4,4-tetrakis (trifluoromethyl)-1,3-dithietane which is a stable liquid (b.p. 110° C.). Hexafluorothioacetone may be conveniently generated from its dimer by thermal cracking which may be readily accomplished by passng the dimer through a hot tube at about 590°-600° C. The dimer, in turn, is rapidly formed from hexafluorothioacetone at about room temperature and the dimerization is catalyzed by bases. Alternatively, hexafluorothioacetone may be prepared by reacting sulfur and hexafluoropropene over a carbon bed at about 400° C. and the hexafluorothioacetone produced can be used immediately after it has been prepared. The effluent gases from such reaction containing hexafluorothioacetone, unreacted hexafluoropropene and by-products should be passed through traps maintained at 150° C. to remove unreacted sulfur. The presence of sulfur lowers the yield of hexafluoroisobutylene from the reaction of ketene with hexafluorothioacetone. These gases are then contacted with ketene to form hexafluoroisobutylene. The total effluent should then be passed through caustic traps to remove residual amounts of ketene and hexathioacetone. This procedure eliminates the need to isolate and purify the hexafluorothioacetone dimer.

Some toxic by-products are produced in the synthesis of hexafluorothioacetone. Perfluoroisobutylene is formed in a significant amount and its presence in the product gas stream seems to be unavoidable. For this reason, cold traps to contain the crude product should contain methanol which rapidly reacts with perfluoroisobutylene at room temperature without seriously affecting the yield of hexafluoroisobutylene.

Elevated temperatures are required for the process of the invention. Reaction temperatures are not critical but generally the reaction should be conducted at temperatures within the range of about 300°-800° C. The preferred temperature range is from about 300°-650° C. and still preferably from 400°-600° C.

Residence time of the reactants is not critical, however, residence times should generally be in the range of about 1-180 seconds. The preferred residence times are from about 5-12 seconds.

The mole ratio of the reactants is not critical, however, ketene is preferably present in at least an equimolar amount and, still preferably, in moderate molar excess. There is no particular advantage in the ketene reactant being present in a molar ratio greater than 2:1. The preferred molar ratio of ketene to hexafluorothioketone is between about 1.5-2:1.

Any convenient reaction chamber may be employed such as a tube or other vessel. A reaction tube is the preferred vessel and should be constructed of a material which is capable of withstanding the reaction temperatures and which is inert to the reactants and products. These materials include metal such as stainless steel, quartz and glass. A preferred reactor design which has been found to result in minimal plugging consist of a stainless steel tube with an alumina liner which is heated by an electric furnace. Within the reactor tube is positioned a second tube of smaller diameter which extends about one third of the way into the heated zone of the outer reactor tube. The inner tube can function to heat one or both of the reactants or to crack a material which generates one or both of the reactants. A thermocouple well to control temperature is positioned on the outside of the reactor tube.

In an illustrative typical embodiment of the invention, ketene and hexafluorothioacetone are fed into the above-described reactor at 550° C. with the ketene being in a 1.5:1 molar excess. The ketene is generated by feeding diketene into the top of the inner tube wherein it is cracked to generate ketene. The hexafluorothioacetone is fed into the top of the outer reactor tube. A trap at the exit (bottom) of the reactor collects any tarry material and non-volatile products, while the remaining gases are scrubbed with caustic solutiion to remove unreacted ketene and hexafluorothioacetone, and are then dried and collected in a −78° C. cold trap. This trap will contain hexafluoroisobutylene, carbonoxysulfide and other by-products such as $CF_3CH_2CF_3$ and $CS_2$. The crude product mixture can then be distilled and analyzed by gas chromatography. Alternatively, the scrubbers can be eliminated and the product mixture distilled directly.

EXAMPLE 1

Hexafluorothioacetone was prepared by feeding hexafluorothioacetone dimer of 95% purity into a 17 mm ID Vycor tube packed with borosilicate glass rings (7×7 mm) and heating to about 600° C. over a length of 12 inches. The feed rate of dimer was 26 g/h along with a He flow of 0.145 mole/h. Hexafluoroacetone thus prepared was reacted with diketene as described below. The reactor employed was a Vycor tube (20 mm I.D.) which was heated by an electric furnace to 500° C.±10° C. over a length of 20 inches. Within the reactor tube was a second Vycor tube of the same material of smaller diameter (17 mm I.D.) which extended about one third of the way into the heated zone of the outer reactor tube. The volume of the tube between the bottom of the inner tube and bottom of the furnace was 128 cc. A thermocouple well is positioned on the outside of its outer tube. HFTA is fed into the outer tube and diketene is fed into the top of the inner tube at the rate of 8.7 g/h. The molar ratio of diketene to HFTA dimer was 1.43. The reaction was run for 5.75 hours during which time the effluent from the reactor was passed through an air trap to collect non-volatiles, a water trap, two 2.5 N KOH traps, a $CaSO_4$ drying column, a Dry-Ice acetone trap, and a liquid nitrogen trap. The residence time for this reaction was 14.5 seconds and was calculated according to the following equation.

Residence Time (sec.) =
$$\frac{(3600 \text{ sec/h}) (273° \text{ K}) (\text{Volume (cc) reactor})}{(22,400 \text{ cc/mole}) (\text{Temp Reaction °K}) (\text{Total Moles gas/h})}$$

The majority of the gases were collected in the −78° trap (98.8 g) which consisted of a top layer (4.1 g) comprised of mainly $CS_2$, and a bottom layer, which contained (by GC analysis) 56.2 area % hexafluoroisobutylene. This corresponds to an approximate yield of 48% for the reaction of ketene with HFTA.

EXAMPLE 2

Diketene was first cracked to ketene in a separate reactor by passing diketene through a 12" long Vycor tube (11 mm I.D.) packed with glass beads. The rate of ketene generated was 8.9 g/h. The reactor was the same as used in Example 1 except that no caustic scrubbers were employed. The ketene was passed into the top of the inner tube of the reactor. Helium was used to dilute the ketene stream at a rate of 0.03 mole/h. HFTA was generated as described in Example 1 at a rate of 38 g/h with a He flow of 0.12 mole/h and was passed into the reactor. Ketene was reacted with HFTA at 550° C. in the reactor at a 1:1 molar ratio and with a residence time of 14.2 seconds. The trap (−78° C.) yielded 117.2 g which, by GC analysis, 31.8 area % was hexafluoroisobutylene. This is approximately a 26% yield after subtracting losses derived from the thermal cracking of the HFTA dimer. The ratio of diketene to HFTA dimer used was 1:1.

EXAMPLE 3

As in Example 2, diketene and HFTA dimer were pre-cracked and ketene and HFTA were fed into a reactor as described in Example 1 and reacted at 520° C. The flow rates were 0.4 moles/h ketene; 0.03 moles/h He in ketene; 0.2 moles/h HFTA; 0.03 moles/h He in HFTA. The volume of the reactor was 45 cc, affording a residence time of 4.2 sec. The ratio of ketene to HFTA was 2:1. After a run of 6 hours, the gases which collected in the −78° trap after passing through the trap system consisting of an air trap, two caustic scrubbers, a $CaSO_4$ drying column, a dry-ice acetone trap and a liquid nitrogen trap, weighed 117.0 g and contained 33.9% hexafluoroisobutylene by GC analysis corresponding to approximately a 35% yield.

EXAMPLE 4

A 1"×28" stainless steel tube fitted with a thermocouple well was heated in an electric furnace to between 561° and 612° over a length of 16", 12" of which was at least at 600° C. Vapors of diketene and HFTA dimer were passed into the reactor at the rate of 11 g/h and 14 g/h, respectively, with a He flow of 0.25 mole/h. The traps consisted of an air trap, ice trap, and two −78° traps. The contents of the latter contained hexafluoroisobutylene as indicated by gas chromatographic, infrared and nuclear magnetic residence analyses.

EXAMPLE 5

Vapors of acetic anhydride (0.185 mole/h), HFTA dimer (0.033 mole/h) and He (0.05 mole/h) were passed into a Vycor tube (17 mm I.D.) and heated to 600° over a length of 18". After passing the effluent gases through two 10% KOH scrubbers and a $CaSO_4$ column, the gases were collected in a −78° trap. Analysis of the latter by GC indicated the presence of hexafluoroisobutylene.

EXAMPLE 6

Hexafluoropropene and sulfur were reacted in a reactor containing 1275 cc carbon catalyst at 380°–425° C. The feed rates of hexafluoropropene and sulfur were 1.84 mole/h and 2.81 mole/h respectively. The product gases of this reaction, after cooling to 150° C. to remove sulfur, were directly fed into a second reactor. The second reactor was a stainless steel tube (Volume—about 880 cc.) with an alumina liner which was kept at about 500° C. Along with the gases from the first reactor, acetic anhydride was fed into the second reactor at a rate of 1.67 mole/h. During a run of 3.8 hours, during which 1057 g (7.05 mole) hexafluoropropene was passed through, a total of 1298 g of crude product was collected. By GC analysis of the amount of hexafluoroisobutylene present was calculated to be 560 g (3.4 mole).

EXAMPLES 7–12

The process of Example 6 is repeated excepting that the reactants and products are varied as indicated in the following Table. Similar results are obtained, that is to say that hexafluoroisobutylene is produced. The changes in these examples from the process of Example 6 are shown in the following Table.

TABLE

| Example | Ketene or Ketene-Generating Compound | Temperature (°C.) | Residence Time (Seconds) | Mole Ratio Ketene:HFTA |
|---|---|---|---|---|
| 7 | ketene | 300 | 25 | 1:1 |
| 8 | acetone | 650 | 5 | 2:1 |
| 9 | acetic acid | 800 | 1 | 2:1 |
| 10 | isopropenyl acetate | 600 | 12 | 2:1 |
| 11 | acetyl acetone | 500 | 25 | 1.5:1 |
| 12 | diketene | 400 | 180 | 1.5:1 |

We claim:

1. The process for preparing hexafluoroisobutylene which comprises reacting, at elevated temperatures, ketene or a ketene-generating compound with hexafluorothioacetone.

2. The process according to claim 1 in which hexafluorothioacetone is reacted with ketene.

3. The process according to claim 1 in which the ketene-generating compound is acetic anhydride.

4. The process according to claim 1 in which the ketene-generating compound is diketene.

5. The process according to claim 1 in which the elevated temperatures are from about 300°–800° C.

6. The process according to claim 1 in which the elevated temperatures are from about 300°–650° C.

7. The process according to claim 1 in which the elevated temperatures are from about 400°–600° C.

8. The process according to claim 4 in which the elevated temperatures are from about 300°–800° C.

9. The process according to claim 8 which the elevated temperatures are from about 300°–650° C.

10. The process according to claim 9 in which the elevated temperatures are from about 400°–600° C.

* * * * *